United States Patent [19]

Poltz

[11] Patent Number: 4,806,383

[45] Date of Patent: Feb. 21, 1989

[54] METHOD OF APPLYING OPAQUE DENTAL CERMIC MATERIAL TO A METAL STRUCTURE

[75] Inventor: H. Poltz, Erlangen, Fed. Rep. of Germany

[73] Assignee: Dentsply GmbH, Dreieich, Fed. Rep. of Germany

[21] Appl. No.: 18,211

[22] Filed: Feb. 24, 1987

[51] Int. Cl.$^4$ .................. A61C 13/00; A61C 13/09; A61K 6/02; B05D 1/36

[52] U.S. Cl. .......................... 427/2; 106/35; 427/203; 427/204; 427/403; 433/201.1; 433/202.1; 433/206; 433/208; 433/223

[58] Field of Search .................. 427/2, 203, 204, 403; 106/35, 313; 433/201.1, 202.1, 206, 207, 208, 217.1, 222.1, 223

[56] References Cited

U.S. PATENT DOCUMENTS

| | | | |
|---|---|---|---|
| 3,338,732 | 8/1967 | Hollomb | 427/403 |
| 3,880,662 | 4/1975 | Daskalon et al. | 433/202.1 |
| 4,010,048 | 3/1977 | Tesk et al. | 148/26 |
| 4,021,915 | 5/1977 | Rubens | 433/217.1 |
| 4,064,311 | 12/1977 | McLean et al. | 428/434 |
| 4,426,404 | 1/1984 | Shoher et al. | 106/35 |
| 4,461,618 | 7/1984 | Deluca et al. | 433/223 |
| 4,468,251 | 8/1984 | Hausselt et al. | 106/1.13 |
| 4,556,389 | 12/1985 | Ueno et al. | 433/223 |
| 4,557,691 | 12/1985 | Martin et al. | 433/199.1 |
| 4,559,191 | 12/1985 | Arons | 264/56 |
| 4,645,454 | 2/1987 | Amdur et al. | 433/202.1 |
| 4,645,488 | 2/1987 | Matukas | 604/59 |

FOREIGN PATENT DOCUMENTS

0119062 9/1984 European Pat. Off. .

Primary Examiner—Paul Lieberman
Assistant Examiner—Linda D. Skaling
Attorney, Agent, or Firm—David E. Wheeler; Edward J. Hanson, Jr.

[57] ABSTRACT

A method of building a dental appliance and a kit for use in the method are provided. In the method, metal copings are coated with an opague ceramic paste, and a coarse ceramic powder, having structural stability under the conditions needed to fire the ceramic paste, is dusted on the coating of ceramic paste, and the coping is fired. A coated metal coping with a rough, sandpaper like surface is produced, and subsequent layers of ceramic paste are applied to the rough surface to build up the dental appliance. The kit of the invention provides at least one preformed opaque ceramic paste, dusting powders, and other ingredients needed to build a dental appliance.

9 Claims, No Drawings

METHOD OF APPLYING OPAQUE DENTAL CERMIC MATERIAL TO A METAL STRUCTURE

BACKGROUND OF THE INVENTION

An opaque dental ceramic (porcelain) paste for applying to dental substructures, to be used in the preparation of ceramic dental appliances, such as crowns and bridges, and a method of using the same are provided.

When crowns, bridges and other metal dental substructures (copings) are to be veneered, the dental technician must first apply and fire a layer of opaque ceramic paste. This layer ensures a good bond to the veneering ceramic and, in addition, masks the unfavorable metal color of the substructure which is necessary to obtain a good aesthetic appearance.

Before the application of the opaque paste, an opaque slurry may optionally be fired on. For this purpose a thin suspension of ceramic opaque is mixed, applied and fired.

Conventional opaque ceramic paste consists of a pulverized opaque ceramic powder which is mixed with water, or a special modeling liquid, by the dental technician. The opaque powder itself consists of ground glass frits, which, owing to their chemical compositions can be melted at temperatures below 1000° C. and opacifying agents. During firing, leucite is partially crystallized out, thus the thermal expansion of the glass is adapted to the thermal expansion of the metal. A high portion of opacifiers ensures a good masking of the dark metal. The opaque materials are sold in several shades since they form the color basis for the desired tooth shade.

In preparing the opaque ceramic paste, the dental technician must adjust the consistency of the paste to obtain a paste which is sufficiently viscous so as to adhere to the metal substructure without sagging, but not so viscous that it cannot be easily applied. This procedure involves much trial and error and is very time consuming.

Conventional opaque application requires much time and skill because a very even layer thickness has to be achieved. If the layer of ceramic opaque is too thin, the metal substructure shines through, when the opaque is too thick, there is not enough space left for the full application of the subsequent body and enamel layers, which results in a diminished aesthetic affect.

Accordingly, there is a need in the art for an opaque paste, and a method, which makes it possible to avoid the time consuming procedure of mixing the paste in the laboratory, and makes it possible to apply opaque ceramic paste more easily and more consistently, using fewer steps, to dental substructures and whereby an even layer thickness is achieved.

SUMMARY OF THE INVENTION

The present invention provides a method for coating a metal substructure for a dental appliance which comprises applying an opaque ceramic paste to the metal substructure, dusting the applied opaque paste with a coarse ceramic powder having an average grain size of from about 40 $\mu$m to 100 $\mu$m, firing the opaque, and applying additional ceramic and firing as needed. The ceramic powder used for the dusting must have a thermal stability such that grain structure is maintained under the conditions of firing. The method may comprise the additional step of using a preformed paste made by mixing a ceramic powder with an organic liquid such as glycerol. At least one additional layer of ceramic paste may then be added to the fired opaque, and said additional layer may optionally be applied using a paste made by mixing a ceramic powder with an organic liquid. Preferably the ceramic paste will be pre-formed and will be loaded into a package in which it can be stored, and from which it can be easily dispensed.

A kit is also provided which contains the preformed, ready to use opaque paste, the coarse ceramic powder, and optionally other ceramic materials that are needed to complete the building of a dental appliance.

Using the method, preformed paste, and the kit of the invention, it is possible for the dental technician to build a dental appliance such as a crown or a bridge using fewer steps, less time and less tedious methods. The preformed paste provided eliminates the need for time consuming trial and error mixing of a paste in the laboratory. The assured quality control of the paste that is used, and the method in which it is used lessens the possibility of applying an opaque layer that is too thin or too thick.

THE PRIOR ART

U.S. Pat. No. 4,064,311, to McLean et al, teaches a process for a ceramic article which comprises firing porcelain onto a metal substrate. The metal substrate has an adherent layer of metal oxide deposited thereon which is wetted by the porcelain in the fused state.

U.S. Pat. No. 4,557,691, to Martin et al, teaches an opaque porcelain paste comprising an opaque porcelain powder mixed with an aqueous colloidal dispersion of urethane polymer. The paste can be applied as the first layer to a dental coping, and does not need to be fired prior to the addition of the body porcelain layers.

European Patent Application No. 0,119,062 teaches a storable paste-like material for use in preparing porcelain dental prostheses comprising a porcelain powder, water, and a small amount of finely divided ceramic material that overcomes the natural separation of the mixture of porcelain powder and water.

DETAILED DESCRIPTION OF THE INVENTION

The ceramic powders used in the present invention broadly constitute a known class of compositions. Conventionally, the powders used in making dental ceramic pastes have a grain size below about 60 $\mu$m. In the ceramic powder used in the paste of the present invention, grain size is kept below about 50 $\mu$m and preferably below about 40 $\mu$m and in addition, powders of a grain size less than about 2 $\mu$m are mixed therewith. Powders having an average grain size in the range of about 40 to 100 $\mu$m are used in a dusting step.

In the method of the invention, either the powder used to make the opaque ceramic paste is ground to a finer grain size than usual, or a portion of very fine powder having a grain size below about 2 $\mu$m is added to the opaque ceramic powder, such that between about 10% and 20% of the ceramic powder comprises a ceramic powder having a grain size below about 2 $\mu$m. In the case where very fine powder is added to the opaque ceramic powder, the fine powder added can be a very fine opaque frit or an opacifier such as $CeO_2$, $ZrSiO_4$, $SnO_2$, $ZrO_2$, or $TiO_2$ or mixtures thereof. As these opacifiers are supplied by the manufacturers in very small grain size, they need not be ground again.

In the method of the invention, the opaque powder is mixed with an organic liquid having a boiling point below 300° C. to form a paste. The organic liquid used should not extend the firing times required and should not generate any hazardous gases during firing. Organic liquids that may be used in the method of the invention may be selected from the glycerols, glycols, derivatives thereof, or dimethylsulfoxide. Particularly preferred is glycerol. Additives that increase the viscosity of the paste, such as alginates and stabilizing salts can be used. The consistency of the paste must be adjusted so that it can be applied to a metal substructure in an even layer with one stroke of the brush.

Using the paste of the invention as described eliminates the need for multiple application of the opaque slurry and firing steps as described in the prior art.

For convenience, it is preferred that the opaque ceramic paste be preformed and packaged in tubes or syringes so that required quantities can be easily extruded by the technician. Pre-forming the paste at the factory ensures that a paste having a specific viscosity and composition for the purpose it is to be used is consistantly produced, thus avoiding the time consuming preparation of the paste in the laboratory. The addition of or presence of the fine grain particles, i.e. below 2 $\mu$m in diameter, helps prevent separation of the organic liquid from the dental powder in the paste while it is being stored and improves the spreadability of the paste.

After a layer of paste has been applied, the coated substructure is dusted with a layer of coarse ceramic powder, having an average grain size of between about 40 $\mu$m and 100 $\mu$m. In the dusting step, the coarse ceramic powder is taken up with a wide, dry brush. The brush is tapped above the object and the coarse grains of powder are thus released onto the freshly applied paste. Other means of providing a dusting will be apparent to those skilled in the art.

The coarse ceramic powde used preferably is chosen such that it has thermal stability under the conditions required for firing the ceramic paste composition. That is, the coarse grains will have properties such that they will form a strong sintered bond with the ceramic paste when the substructure is fired, but the grains will not be significantly melted or distorted by tthe firing so that a coarse grainy surface similar to that of sandpaper will be obtained.

Alternatively, when extra large grains of powder are ued in the dusting step, ceramic powders may be chosen having a thermal stability such that a substantial portion of the grain structure is retained during firing, so that the sandpaper consistency of the surface, described above, is obtained.

A second layer of ceramic paste may then be applied to the substructure, filling the gaps between the protrusions of the coarse grains on the surface of the ceramic opaque, and fired.

As is known to those skilled in the art, the first paste layer used may be made especially opaque, in order to completely mask the metal which it covers, and formulated to form a good bond with the metal. The second layer may be shaded according to the desired tooth shade. Dentin and enamel layers may be added in due course.

The coarse ceramic grains distributed on the first layer of ceramic opaque simplifies the addition of the second layer of ceramic paste since the technician need only concentrate on filling the gaps between the grains to achieve an even layer. Further, like bricks in a wall that overlap end to end, the grains serve as posts or anchors to improve the bonding of the next layer of ceramic.

In the second layer of opaque paste, which is applied to the spaces between the coarse grains, the use of additional opacifying oxides such as $TiO_2$ or $SnO_2$ in the composition is not desirable because of their high opacifying effect. To prevent separation of the dental powder from the modeling liquid in the paste used in the second layer, it is preferred that about 3% of a hydrophobic aerosil (such as Degussa R 972) be added to the organic liquid (preferably glycerol). The spreadability of this paste is not as good as that of the first layer because of the absence of the fine (less than 2 $\mu$m) particles, but high spreadability of the second layer is not needed because application of the second layer is made easy because of the presence of the coarse grains fired on to the first layer of paste.

The rough surface, resulting from the use of the coarse ceramic particles, can also be used in the case where a silane bonding agent is used for applying and polymerizing an acrylic resin veneer. The present method can also be used in the adhesive bonding technique. Both methods are well known in the art.

The method of the present invention has the advantages that it saves the dental technician considerable time, because application of the different layers of paste is made easier. There is less waste of material because the technique is simplified and the time spent on trial and error mixing of the paste in the laboratory is substantially eliminated. The opaque layers may be made especially thin and even, thus leaving enough room for body and enamel layers so that a good aesthetic result can be obtained. Also, since the technique is made simple, and more even layers are obtained, the possibility of faults developing is reduced.

As an example of the composition that may be used for the first opaque layer, the following is provided:

EXAMPLE

Composition of the opaque for the first layer:

| | |
|---|---|
| $SiO_2$ | 42 weight % |
| $Al_2O_3$ | 12 weight % |
| $K_2O$ | 8 weight % |
| $Na_2O$ | 4 weight % |
| $Li_2O$ | 0.5 weight % |
| CaO | 1.5 weight % |
| $B_2O_3$ | 1 weight % |
| $ZrO_2$ | 1 weight % |
| $SnO_2$ | 10 weight % |
| $TiO_2$ | 20 weight % |

All oxides are ingredients of a ground glass frit. Only the $TiO_2$ is admixed to insure the presence of a fine powder, which is needed to insure the good spreadability of the paste.

The composition of the opaque paste for the second layer will differ slightly from the above formula because part of the opacifiers will be replaced by pigments in order to produce the desired tooth shade.

The opaque, not including the $TiO_2$, has the following grain size distribution:

| <5 | <12 | <24 | <40 | um |
|---|---|---|---|---|
| 21 | 66 | 98 | 100 | % |

On the average, $TiO_2$ has a grain size less than about 1 μm.

The paste has the following composition:

| | |
|---|---|
| opaque powder | 67.7 weight % |
| glycerol | 32.0 weight % |
| alum or other stabilizing salt | 0.3 weight % |

The coarse ceramic powder distributed on the opaque paste after it is applied to the dental appliance substructure has the following composition:

| | |
|---|---|
| $SiO_2$ | 56 weight % |
| $Al_2O_3$ | 13 weight % |
| $K_2O$ | 9 weight % |
| $Na_2O$ | 4 weight % |
| $CeO_2$ | 18 weight % |

The sieve fraction used: <80 μm >40 μm

The paste and dusting powder described in the Example will be fired at about 980° C.

For convenience, the materials used in the method of the invention may be provided in kit form.

The preformed opaque paste, with known firing properties, may be packaged in a kit with a coarse ceramic powder that has the thermal stability required by the present method under the firing conditions required to fire the pre-formed paste. If more than one ceramic paste having different properties for different applications, and having different firing requirements, and more than one coarse ceramic powder are provided in the same kit, the packages containing them can be color coded so that the correct coarse ceramic powder is used with the correct ceramic paste. As will be apparent to those skilled in the art, many specific ceramic compositions may be matched with many specific dusting powders by comparing physical properties that are known in the art.

In addition to the opaque paste, the kit may be provided with additional ceramics for use in the body layers and the dentin and enamel layers and other conventional materials as required. To the degree possible, these materials may be provided in a preformed paste, or in conventional states. For example, as described above, a paste composition of the second opaque layer may be provided.

While specific embodiments of the invention have been described herein, it will be apparent to those skilled in the art that the present invention may be modified and variously practiced without going outside the scope of the following claims.

What is claimed is:

1. A method for coating a metal structure for a dental appliance consisting essentially of the steps of: preparing an opaque ceramic paste by mixing an opaque ceramic powder with an organic liquid having a boiling point below about 300° C., coating said metal structure with said opaque ceramic paste to prepare a coating of opaque ceramic paste on said metal structure, dusting said coating with a coarse ceramic powder having an average grain size of from about 40 μm to about 100 μm said powder having thermal stability such that at least a substantial part of grain structure of said powder is maintained under conditions of firing said dental appliance, applying at least one additional layer of ceramic opaque paste, and firing said dental appliance.

2. The method according to claim 1 in which said organic liquid is selected from the group comprising glycerol, glycol, or dimethylsulfoxide.

3. A method according to claim 2 in which said organic liquid is glycerol.

4. The method according to claim 1 in which said ceramic paste contains about 10% to 20% by weight $SnO_2$, $CeO_2$, $TiO_2$, $ArO_2$, $ZrSiO_4$ or mixtures thereof, having a particle size less than about 2 μm.

5. A method according to claim 1 in which said ceramic powder used in said first opaque paste comprises grains having a particle diameter of less than about 40 μm.

6. The method according to claim 1 which comprises the further step of loading said ceramic paste into a package in which it can be stored and from which said paste can be put directly into use.

7. The method according to claim 6 in which said package is a syringe.

8. The method according to claim 1 which comprises the step of applying a second layer of opaque paste in such a manner that the gaps between projecting grains of coarse ceramic material are totally filled.

9. The method according to claim 1 in which said firing is a vacuum firing.

* * * * *